United States Patent [19]

Crovella et al.

[11] 4,121,573

[45] Oct. 24, 1978

[54] WIRELESS CARDIAC MONITORING SYSTEM AND ELECTRODE-TRANSMITTER THEREFOR

[75] Inventors: Edward A. Crovella, Snyder; Frederick R. Mellon, Clarence, both of N.Y.

[73] Assignee: Goebel Fixture Co., Hutchinson, Minn.

[21] Appl. No.: 648,778

[22] Filed: Jan. 13, 1976

Related U.S. Application Data

[63] Continuation of Ser. No. 403,497, Oct. 4, 1973, abandoned, which is a continuation of Ser. No. 152,516, Jun. 14, 1971, abandoned.

[51] Int. Cl.² .............................................. A61B 5/04
[52] U.S. Cl. ............................ 128/2.1 A; 128/2.06 E
[58] Field of Search ................... 128/2.06 D, 2.06 B, 128/2.06 E, 2.06 F, 2.06 G, 2.06 R, 2.1 A, 2.1 P, 2.1 R, 419 C, 419 E, 419 P, 419 R

[56] References Cited

U.S. PATENT DOCUMENTS

| | | | |
|---|---|---|---|
| 3,212,496 | 10/1965 | Preston | 128/2.1 A |
| 3,253,588 | 5/1966 | Vuilleumier et al. | 128/2.1 A |
| 3,534,728 | 10/1970 | Barrows | 128/2.06 R |
| 3,587,565 | 6/1971 | Tatoian | 128/2.06 E |
| 3,699,389 | 11/1970 | Holsinger | 128/2.1 P |

FOREIGN PATENT DOCUMENTS 1,008,027  10/1965  United Kingdom ................ 128/2.1 A

*Primary Examiner*—William E. Kamm
*Attorney, Agent, or Firm*—Joseph P. Gastel

[57] ABSTRACT

A system for monitoring a cardiac patient comprising an unit having a pair of spaced electrodes mounted on a resilient base which also carries a transmitter connected to the electrodes, and a receiver-adapter for receiving the transmitted signal from the transmitter, said receiver-adapter being coupled to a conventional display device, such as an oscilloscope.

5 Claims, 8 Drawing Figures

U.S. Patent   Oct. 24, 1978   Sheet 1 of 2   4,121,573
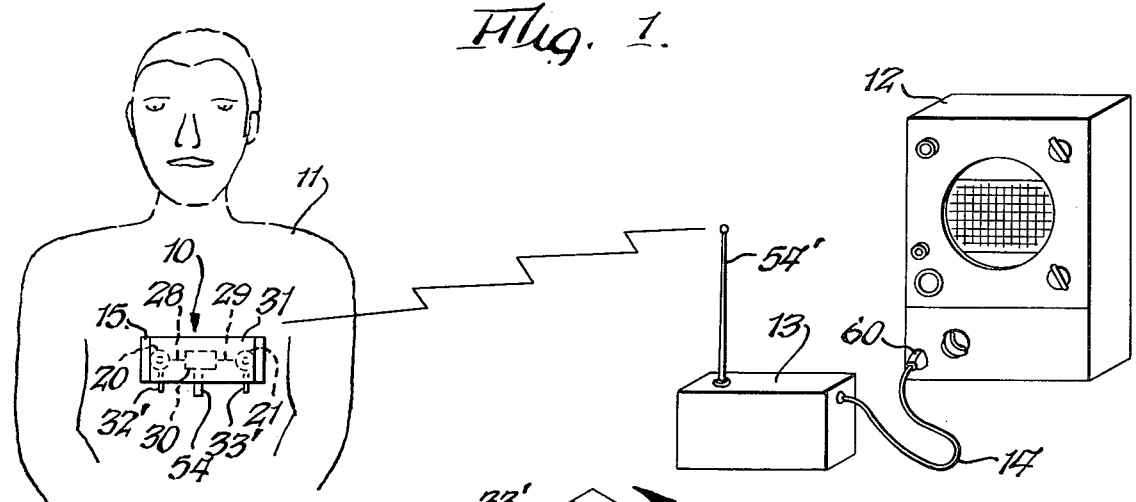
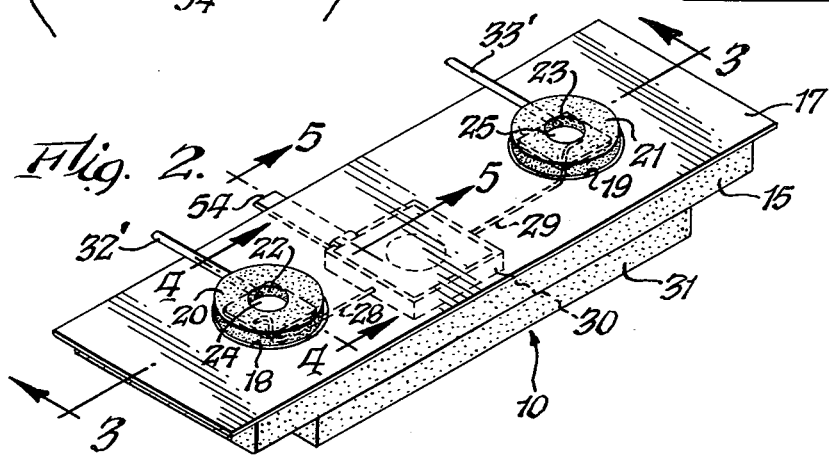
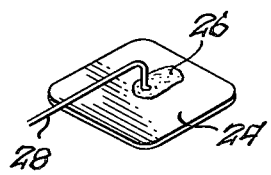
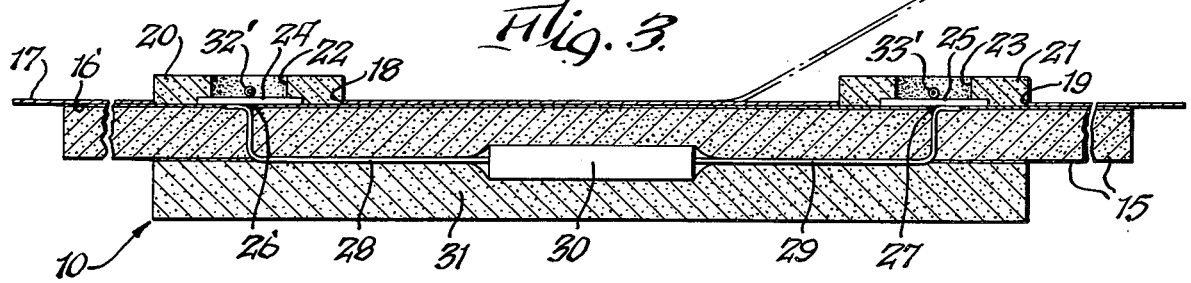
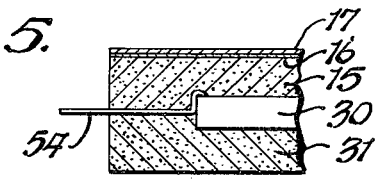
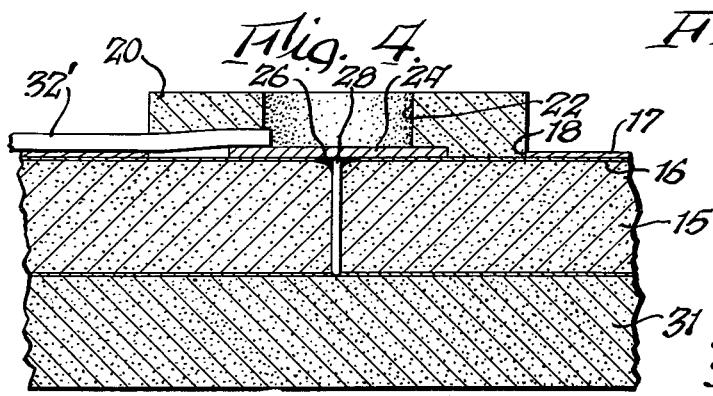
INVENTORS
Edward A. Crovella
Frederick R. Mellon
BY Sommer, Weber & Gastel
ATTORNEYS

4,121,573

WIRELESS CARDIAC MONITORING SYSTEM AND ELECTRODE-TRANSMITTER THEREFOR

This is a continuation, of application Ser. No. 403,497 filed on Oct. 4, 1973, now abandoned which is a continuation of Ser. No. 152,516, filed on June 14, 1971, now abandoned.

The present invention relates to an improved cardiac monitoring system which includes an electrode-transmitter unit and a receiver-adapter for applying the transmitted signal to an existing display device which produces a visual representation of a patient's heartbeat.

In the past monitoring of cardiac patients has been deficient in a number of respects. First of all, practically all monitoring requiring that the patient be connected to an electrical source which not only confined his movement and created anxiety because of the existence of wires but also subjected him to the hazard of electrical shock. Furthermore, prior equipment was generally used and reused thereby requiring maintenance and cleaning before being placed on a new patient. It is with overcoming the foregoing deficiencies of the prior art that the present invention is concerned.

It is accordingly one important object of the present invention to provide an improved cardiac monitoring system which includes a disposable self-contained, wireless electrode-transmitter unit which may be applied to a patient in a simple manner and an adapter for receiving a transmitted signal therefrom and feeding it into a conventional preexisting display device. A related object of the present invention is to provide an arrangement for converting existing cardiac monitoring equipment which requires a wire connection to a patient to one which can provide a display of the cardiac patient's heartbeat without being connected thereto by wires.

Another object of the present invention is to provide an improved electrode-transmitter unit which can be attached to a patient in a simple manner by pressure-sensitive adhesive thereon and which will provide a highly stable, low-cost circuit making it suitable for disposable use, thereby obviating the necessity for cleaning the apparatus between use by different patients and also eliminating any maintenance thereon.

A further object of the present invention is to provide a radio transmitter which is highly miniaturized for transmitting a heartbeat, but which will not drift significantly in spite of its small size.

Yet another object of the present invention is to provide a cardiac electrode-transmitter package which has all wires concealed internally and therefore will not snag on foreign objects and which is of sufficiently low power that interference with other equipment is minimal. Other objects and attendant advantages of the present invention will readily be perceived hereafter.

The improved system for monitoring a cardiac patient comprises electrode means adapted to be placed in electrical contact with the patient, a transmitter mounted on the patient and coupled to the electrode means for transmitting a signal representative of the patient's heartbeat, display means for providing a trace of the patient's heartbeat and adapter means coupled to the display means for receiving the signal and conducting it to the display means. The improved electrode-transmitter unit comprises a pair of spaced electrodes with a transmitter connected thereto mounted on a resilient pad.

The various aspects of the present invention will be more fully understood when the following portions of the specification are read in conjunction with the accompanying drawings wherein:

FIG. 1 is a schematic representation of the improved system of the present invention;

FIG. 2 is a perspective view of the improved electrode-transmitter of the present invention;

FIG. 3 is an enlarged fragmentary cross-sectional view taken substantially along line 3—3 of FIG. 2;

FIG. 4 is an enlarged fragmentary cross sectional view taken substantially along line 4—4 of FIG. 2;

FIG. 5 is an enlarged fragmentary cross sectional view taken substantially along line 5—5 of FIG. 2;

FIG. 6 is a fragmentary perspective view of the plate which forms the electrode;

Figure 7:
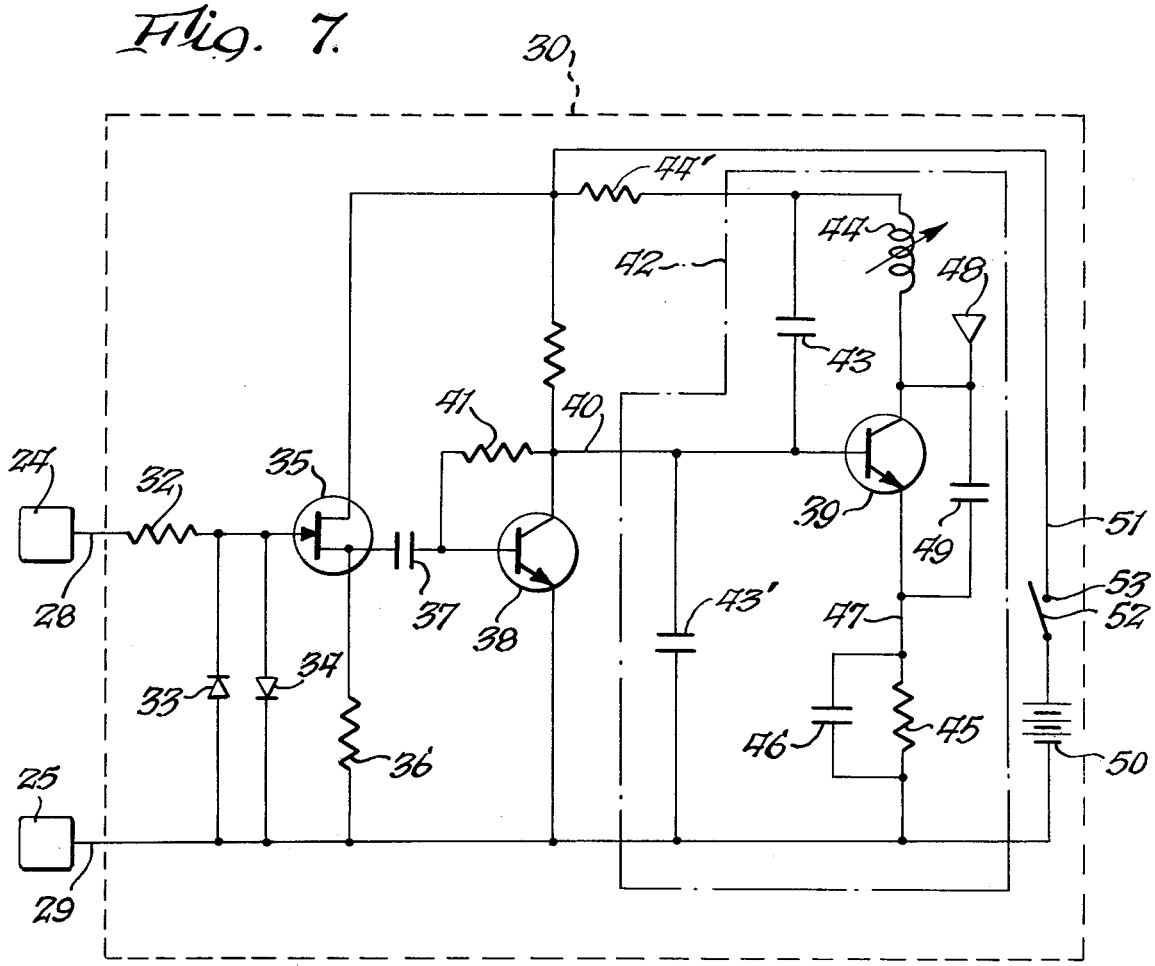
FIG. 7 is a schematic wiring diagram of the improved transmitter circuit.
Figure 8:
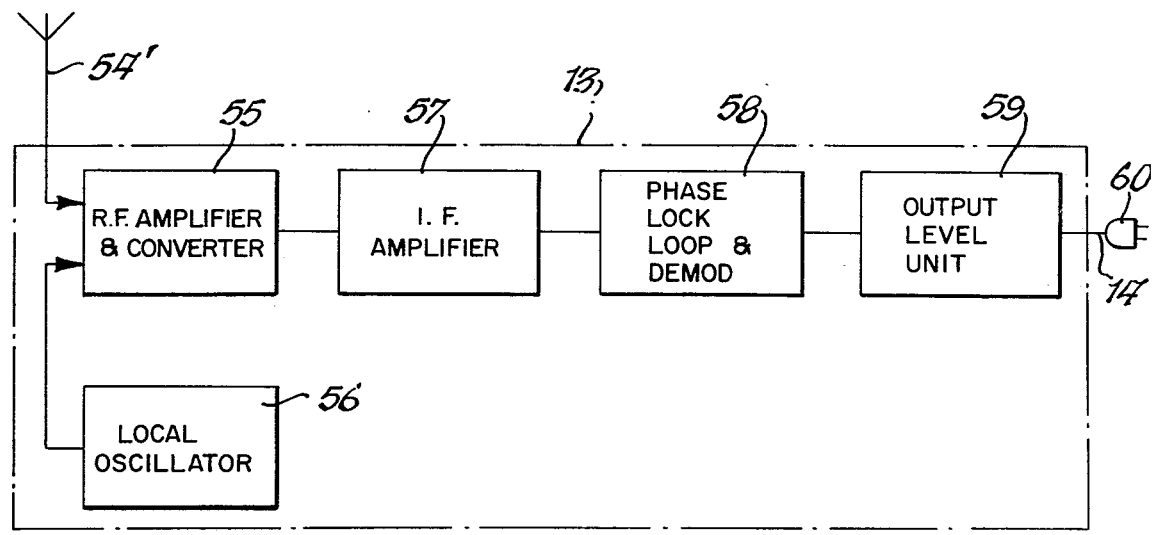
FIG. 8 is a block diagram of the adapter for receiving the transmitted signal and conveying an output to the display device.

The improved system of the present invention as shown in FIG. 1 includes an electrode-transmitter unit 10 adapted to be adhesively secured on cardiac patient 11, a display device, such as oscilloscope 12, for providing a pictorial representation of the patient's heartbeat, and an adapter 13, which is essentially a radio receiver for receiving the signal transmitted from electrode-transmitter unit 10 and converting it to an output which is fed into display device 12 via lead 14.

The improved electrode-transmitter unit 10 includes a first flexible resilient foam-like pad 15 made out of polyurethane. Pad 15 has a pressure-sensitive adhesive 16 applied thereto which is covered by a protective paper covering 17. The pad 15 with the adhesive layer 16 with the paper covering 17 can be obtained commercially under the trademark RESTON of the 3M Company. Cutouts 18 and 19 are provided which are in contiguous relationship to raised annular wells 20 and 21 having apertures 22 and 23, respectively, therein for receiving electrode jelly. Interposed between annular wells 20 and 21 and pad 15 are metallic electrodes 24 and 25 which are fabricated from silverchloride, German silver, or any other suitable conductor. As can be seen from FIGS. 2, 3 and 4, annular wells 20 and 21 have inner portions which overlie the outer edges of the electrodes 24 and 25 to securely hold them in position considering that wells 20 and 21 are secured to pad 15 through the adhesive 16 on the face of the latter. Connected to electrodes 24 and 25 by means of solder 26 and 27, respectively, are leads 28 and 29, respectively, which emanate from transmitter 30 which is held in position on unit 10 by means of a second resilient foam pad member 31, such as polyurethane, which is adhesively secured to pad member 15. Communicating with wells 22 and 23 are tubes 32' and 33', respectively, having outer ends for receiving a syringe containing electrode jelly. These tubes conduct this electrode jelly to apertures 22 and 23 after the pad has been adhesively secured to the chest of the patient in the manner shown in FIG. 1.

In order to secure unit 10 to the chest of the patient, it is merely necessary to strip the protective paper backing 17 from unit 10 so as to expose pressure-sensitive adhesive 16 and thereafter merely press the unit 10 in position on the chest of the patient with the outer surfaces of annular walls 20 pressing against the chest, after which the wells are filled with electrode jelly through tubes 32' and 33'.

In view of the fact that the electrode and the transmitter is a self-contained unit without any wires leading to display device 12, the patient is unhampered in his movement, that is, he is not physically attached to any external source. Furthermore, and more importantly the patient is afforded a high degree of safety in that he is not connected to electrical apparatus which can malfunction and possibly provide him with electric shock or in the extreme case electrocute him. It is further to be noted that since all of the hard elements of unit 10 are effectively sandwiched between resilient pads, the patient can generally lie on the unit 10 without suffering discomfort.

The improved transmitter 30 which is mounted on unit 10 is actually extremely small, approximately 1 inch square and a third of 1 inch high. The circuit includes leads 28 and 29 which are coupled to electrodes 24 and 25 as noted above. Resistor 32 in lead 28 provides protection to the remainder of the transmitter circuit by providing a high voltage drop for preventing defibrillating voltages which may be applied to the patient from being transmitted to the remainder of the circuit. Further in this respect diodes 33 and 34 protect the remainder of the transmitter because they will conduct when a voltage in excess of ½ volt is applied across leads 28 and 29.

Also coupled across leads 28 and 29 is an input amplifier consisting of a field effect transistor 35 which is biased relative to lead 29 by means of resistor 36. The transistor 35 essentially provides a high impedance buffer stage which gives a high input impedance so that good signal transfer from the electrodes 24 and 25 is obtained because of the high magnitude of this high impedance relative to the impedance produced between electrodes 24 and 25 by the patient.

The output signal from transistor 35 is conducted through capacitor 37 which transfers the AC signal but blocks the DC signal. Thereafter the signal is fed to amplifying transistor 38 which constitutes a first stage amplification of the patient's heartbeat and sets the DC bias on transistor 39, the amplified signal being conducted to transistor 39 through lead 40 with resistor 41 providing a feedback to bias transistor 39 and effect stabilization thereof. Transistor 39 forms a part of voltage control oscillator 42 which is essentially a modified Colpitts oscillator. The DC voltage which is applied to the base of transistor 39 from transistor 38 controls the frequency of the oscillator. Capacitors 43-43' and variable inductor 44 comprise the tuned circuit of the oscillator. Resistor 44' biases transistor 39. Resistor 45 and capacitor 46 in lead 47 are a DC bias resistor and an emitter bypass capacitor, respectively. The antenna 48 is connected across transistor 39 as shown to provide a feedback circuit through capacitor 49. The antenna 48 is a conductor printed on a circuit board and therefore is not external to the unit shown as the box 30 in FIGS. 2 and 3.

As can be seen from FIG. 7, a battery 50 is effectively coupled between leads 51 and 29 through normally open switch 52. In this respect it is to be noted that actually switch 52 includes a spring-biased armature which is separated from contact 53 by means of a plastic insulating tab 54 which is pulled out of the transmitter so as to cause armature 52 to engage contact 53 when it is desired to activate transmitter 30. The circuit shown in FIG. 7 provides an output of between 38 and 42 megacycles with a field strength of under ten microvolts per meter at fifty feet.

The above described unit 10 including the transmitter is a low-cost unit which can be disposed of after it has served its purpose. In this respect the battery can cause it to operate for a period of 7–10 days before it expires. Because it can stay on the patient for this length of time, the nurse does not have to change it during its useful life. Furthermore, because it is disposed of after its useful life has terminated, there is no problem due to the use of faulty equipment which has not been properly maintained. Additionally, there is no sanitation problem which could arise from transferring the unit from one patient to another because of the fact that the unit is disposed of after use. Also limiting the power of the transmitter, as noted above, lessens the possibility of interference with other electrical equipment.

Adapter 13 is a conventional receiver which includes an antenna 54' coupled to RF amplifier and converter 55 which is also coupled to local oscillator 56. The output from the amplifier is fed to the IF amplifier 57 which in turn is fed to a conventional phase-lock loop and demodulator 58 which is in the form of an integrated circuit. The output is then fed to the output level unit 59 which maintains the signal at a desired level and the signal is then fed to lead 14 having a plug 60 at the end thereof which attaches to the display device 12.

By the use of adapter 13 an existing display device, such as oscilloscope 12, may be used to display the signal which is transmitted from patient 11. This obviates the necessity for hospitals and other cardiac care facilities to replace existing display devices when they adopt the system of the present invention. It will be appreciated that adapter 13 can be used with any display device in addition to an oscilloscope.

While a preferred embodiment of the present invention has been disclosed, it will be appreciated that it is not limited thereto but may be otherwise embodied within the scope of the following claims.

What is claimed is:

1. An electrode transmitter combination for monitoring the heartbeat of a cardiac patient comprising base means including first and second pad means, first and second surfaces on said first pad means, third and fourth surfaces on said second pad means, said first and second pad means being oriented with said second and third surfaces in contiguous relationship, spaced electrode means proximate said first surface for engagement with the chest of said patient, self-contained transmitter means positioned between said second and third surfaces, lead means coupling said transmitter means to said electrode means, and means for adhesively securing said base means to the chest of said patient.

2. An electrode-transmitter combination for monitoring a cardiac patient as set forth in claim 1 including means for spacing said electrodes from the surface of the chest of said patient while maintaining them exposed to said chest.

3. An electrode-transmitter combination for monitoring a cardiac patient as set forth in claim 2 wherein said transmitter means is spaced between said electrodes.

4. An electrode-transmitter combination as set forth in claim 3 wherein said means for adhesively securing said base means to the chest of said patient comprises pressure sensitive adhesive on said first surface.

5. An electrode-transmitter combination for monitoring a cardiac patient as set forth in claim 4 wherein said transmitter means includes a battery for providing a power source therefor, and means maintaining said battery effectively uncoupled from said transmitter means and for permitting coupling of said battery to said transmitter means from outside of said pad means.

* * * * *